United States Patent
Tengvall et al.

(12) 
(10) Patent No.: US 6,379,976 B1
(45) Date of Patent: Apr. 30, 2002

(54) DETERMINATION OF POLYMERIZATION/COAGULATION IN A FLUID

(75) Inventors: Pentti Tengvall; Ingemar Lundstrom, both of Linkoping (SE)

(73) Assignee: Global Hemostasis Institute MGR AB, Linkoping (SE)

( * ) Notice: Subject to any disclaimer, the term of this patent is extended or adjusted under 35 U.S.C. 154(b) by 0 days.

(21) Appl. No.: 09/622,063

(22) PCT Filed: Feb. 23, 1999

(86) PCT No.: PCT/EP99/01156

§ 371 Date: Nov. 14, 2000

§ 102(e) Date: Nov. 14, 2000

(87) PCT Pub. No.: WO99/44060

PCT Pub. Date: Sep. 2, 1999

(30) Foreign Application Priority Data

Feb. 26, 1998 (SE) ............................................... 9800590

(51) Int. Cl.⁷ ..................... G01N 33/53; G01N 33/543; G01N 33/00; G01N 33/48; G01J 3/45
(52) U.S. Cl. ........................... 436/518; 436/63; 436/66; 436/69; 436/805; 422/68.1; 422/73; 422/82.01; 356/39; 356/73.1; 356/318; 356/445; 356/455
(58) Field of Search ................................ 336/455, 445, 336/318, 39, 73.1; 436/63, 66, 69, 805, 518; 422/68.1, 73, 82.01

(56) References Cited

U.S. PATENT DOCUMENTS 5,656,504 A * 8/1997 Johansson et al. .......... 436/518
5,658,723 A   8/1997 Oberhardt ..................... 435/4
5,670,329 A   9/1997 Oberhardt ................... 435/13

FOREIGN PATENT DOCUMENTS

DE         35 22 098 A       1/1987

OTHER PUBLICATIONS

Malmquist et al Current Opinion in Chemical Biology(1997) 1:378–383.*
Bjorquist et al Thrombosis research vol. 85 No. 3 pp. 225–236(1997).*
Nakamura et al anal. Chem.(1997)69 4649–4652.*

* cited by examiner

*Primary Examiner*—Christopher L. Chin
*Assistant Examiner*—Kartic Padmanabhan
(74) *Attorney, Agent, or Firm*—Bacon & Thomas

(57) ABSTRACT

An analytical method of qualitative and optionally quantitative determination of the occurrence of polymerization/coagulation in a fluid containing polymerizable/coagulable components is described. The method comprises the steps of directing incident beams of electromagnetic radiation through a transparent support on which a film of electrically conducting material is placed, to the back of the film, at angles equal to or greater than the critical angle for total reflection, and measuring changes in the reflected beams due to changes in the surface plasmon resonance angle. Repeated measurements are correlated to the occurrence and magnitude of changes with qualitative and optionally quantitative occurrence of polymerization/coagulation in the fluid. The analytical method is not volume dependent since only one (small) surface of the measuring instrument needs to be in contact with the fluid. Further, the method can also be applied to poorly transparent fluids such as blood.

20 Claims, 3 Drawing Sheets

DETERMINATION OF POLYMERIZATION/COAGULATION IN A FLUID

This is the National Stage Filing of PCT/EP99/01156 Filed on Feb. 23, 1999.

The present invention relates to the determination of polymerization/-coagulation in a fluid. More precisely, the invention relates to an analytical method of qualitative and optionally quantitative determination of the occurrence of polymerization/coagulation in a fluid containing polymerizable/-coagulable components.

BACKGROUND OF THE INVENTION

Many processes, technical as well as biological, involve polymerization/-coagulation of polymerizable/coagulable components in a fluid. Examples of such technical processes include curing of paints, lacquers, and glues; production of industrial polymers; and thickening of sauces, custards, mousses, jellies and other food stuff. Examples of such biological processes include coagulation of blood, lymph and synovial fluid, curdling of milk and gelling of agar.

The occurrence of polymerization/coagulation in a fluid has traditionally been determined with methods based on changes in optical or rheological properties of the fluid. Changes in optical properties encompass all changes in how the fluid interacts with visible and infra-red electromagnetic radiation that pass through the fluid. Changes in rheological properties denote changes in the properties of the fluid, such as viscosity, elasticity etc. For a review of prior art methods for the determination of qualitative and quantitative occurrence of polymerization/-coagulation in a fluid, see e.g. G. Odian, Principles of polymerization, Wiley Interscience, New York.

Due to convenience, economy and/or ease of performance, optical methods are often preferred, except when rheological information is specifically required. Rheological methods are used when optical methods are difficult or impossible to perform, as is the case when the fluid has poor transparency for electromagnetic rays of the required wavelength.

Poor transparency may be due either to the presence of suspended particles that scatter the electromagnetic radiation which is beamed through the fluid, or to molecular structures that absorb this radiation. For example, optical determination of the occurrence of polymerization/coagulation is difficult or impossible to use in paints, blood and milk. These, and other important fluids, have poor transparency due to scattering and absorbing pigments, cells and/or lipids. Determination of the occurrence of polymerization/coagulation in such fluids may require the use of less convenient rheological methods. Alternatively, the suspended particles and absorbing molecular structures may be removed from the fluid prior to optical determination, but such removal reduces the convenience of the method and adds uncertainty to the determination.

There are also situations when polymerization/coagulation result in virtually no change in optical properties of the fluid. Such is the case for coagulation in blood plasma from individuals with fibrinogen that forms thin fibers. The same applies to formation of jellies and other food thickening processes that involve polymerization/coagulation of large carbohydrate molecules. In situations like these, optical methods may be difficult or impossible to use, and determination of polymerization/coagulation may need to be performed with more cumbersome rheological methods.

Evidently, there is a need for analytical methods for qualitative and optionally quantitative determination of the occurrence of polymerization/-coagulation in a fluid. Such methods should preferably be as convenient as the prior art optical methods but should be applicable also in fluids with poor transparency and for occurrences of polymerization/coagulation that give rise to no or insufficient changes in the optical properties of the fluid.

It has now surprisingly been found that polymerization/coagulation in a fluid, which may be poorly transparent, can be detected and measured by methods based on changes in the surface plasmon effects which appear when a beam of electromagnetic radiation passes an interface. The surface plasmon is a longitudinal or traverse magnetic (TM) charge-density wave propagating along the interface between the two media. The surface plasmons are particularly pronounced if the interface is between an electrical conductor and a dielectric. A spectacular feature is the appearance of a surface plasmon resonance; an increased energy transfer into the surface plasmon, when a beam of electromagnetic radiation, at a certain angle and under conditions for total reflection, hits the interface. This certain angle is referred to as the surface plasmon angle. An overview of the principles of surface plasmon resonance and details on how this phenomenon may be observed and used for studies of bimolecular binding reactions when one of the binding-partners is attached to the biosensor (metal) surface are given in Liedberg B. and Lundström I., Principles of bio-sensing with an extended coupling matrix and surface plasmon resonance. Sensors and Actuators B. 11 (1993) 63–72, the teachings of which are incorporated herein by reference.

DESCRIPTION OF THE INVENTION

The present invention provides an analytical method of qualitative and optionally quantitative determination of the occurrence of polymerization/-coagulation in a fluid containing polymerizable/coagulable components.

A modified commercial instrument for determination of shifts in surface plasmon resonance angle was used in the experimental part of this description. When a drop of blood plasma was placed on the gold film of the instrument, relatively large effects corresponding to shifts of approximately 0.5 degrees in surface plasmon resonance angle accompanied the coagulation of the blood plasma. When the blood plasma was replaced by whole blood, similar effects were observed as the whole blood coagulated. Even larger shifts in the surface plasmon resonance angle were observed when an acryl amide dissolved in water polymerized.

The analytical method of the invention places small or no requirements on fluid volume, i.e. fluid volume size and precision in fluid transfer need not be of importance for the analytical result. This is because determinations are only effected by the fluid that is in contact with a (small) surface area and only by the fluid that is within a limited distance from this surface area. The (small) area in question is typically 1 $\mu m^2$ to 10 $mm^2$ and the limited distance up to about 1 $\mu m$.

The small requirements on sample volume may be an advantage in relation to the prior art optical and rheological methods which require that the fluid be in special containers, e.g. sample holders and cuvettes. This prior art requirement may be inconvenient or even hinder the determination. For example, in fluids of small volume or in fluids under severe conditions it may be difficult or impossible to properly fill the sample holder or cuvette. Examples of small-volume situations are polymerization/coagulation in a drop of blood or in a precious archeological samples. An example of severe-conditions situation is polymerization/-coagulation inside the high pressure and temperature polymerization reactor, e.g. in the production of polyethylene. On-line determinations, e.g. determinations inside flow through industrial reactors and inside the circulatory system are also difficult or impossible to perform with the prior art methods. The present invention enables determination of the occurrence of polymertzation/coagulation also in the above mentioned situations.

The present invention is in particular directed to an analytical method of qualitative and optionally quantitative determination of the occurrence of polymerization/coagulation in a fluid containing polymerizable/coagulable components, which comprises the steps of a) initiating the polymerization/coagulation in the fluid,
b) bringing the fluid or a sample thereof into contact with a film of electrically conducting material on a support which is transparent for the electromagnetic radiation used and which is more optically dense than the fluid,
c) directing incident beams of electromagnetic radiation through the support, to the back of the film, at angles equal to or greater than the critical angle for total reflection,
d) measuring changes in the reflected beams due to changes in the surface plasmon resonance angle,
e) repeating the steps c) and d) at least once,
f) registering the occurrence and magnitude of the changes measured in d), and
g) correlating the occurrence and magnitude of changes with qualitative and optionally quantitative occurrence of polymerization/coagulation in the fluid.

The steps a), b), and c) may be performed simultaneously or in any alternative order prior to the measurement in step d).

Preferably, especially in an on-line situation, the step e) is performed continuously so that changes in the reflected beam due to changes in surface plasmon resonance angle is continuously registered. This can, for example as with the BIAlite instrument from Biacore AB, Uppsala, Sweden, allow recording of a sensogram plotting arbitrary resonance units against time. However, the measurement of e) may only be performed once, even though several measurements normally will be made. The term continuous could ,in this context, mean once every second, 10 times every second, 100 times every second or as many times per unit of time as is needed for good time resolution of qualitative and quantitative occurrence of polymerization/coagulation in the fluid.

Directing incident beams of electromagnetic radiation through the support, to the back of the film, at angles equal to or greater than the critical angle for total reflection, i.e. in the step c), can be performed in many different ways within the scope of the invention. The beams can be directed continuously or be directed in pulses. The beams can be parallel, convergent or divergent. The beams can illuminate a relatively large area on the back of the film or an area that is arbitrarily small. Parallel beams illuminating a very small area could be conceived as only one beam without departing from the spirit of the invention. The beams can be composed of electromagnetic radiation that is polarized, non-polarized, mono-chromatic or poly-chromatic, coherent, non-coherent or combinations of these properties. The wavelength of the electromagnetic radiation can vary widely. In many embodiments the wavelength is in range the 100 to 2000 nm and thus includes what is referred to as infrared, visible and ultraviolet light.

In situations where the fluid exhibits adsorption at some particular wavelength, it may be advantageous for the incident beams of electromagnetic radiation to be of this, or close to this, wavelength. A reason is, that the surface plasmon resonance may be stronger, i.e. a greater decrease in intensity of the reflected beam at the resonance angle, if the wavelength of the incident light coincides with absorption wavelength(s) of the fluid. Another reason is, that shifts in the surface plasmon resonance angle may be larger if the wavelength of the incident light coincides with the absorption wavelength of the fluid. For example, in analysis of polymerization/coagulation in blood, it may be advantageous to chose a wavelength for the incident electromagnetic radiation that coincides with one of the absorption wavelengths of the red blood cells. This could improve the analysis, by improving signal to noise ratio. The initiation, step a) of the method according to the invention, may in some applications be spontaneous. Particularly this is so when occurrance of spontaneous polymerization/coagulation is to be determined. In such instances, nothing is done in step a), but the subsequent steps of the invention are performed.

In other applications of the invention, the interest may reside in determining how various physical conditions in the fluid influence the qualitative and quantitative occurrence of polymerization/coagulation. The initiation, step a) of the method of the invention, will then consist in changing one or several such conditions. These conditions include, but are not limited to, temperature, pressure, ionic strength, pH and pe (activity of free electrons, a measure of the redox potential of the fluid).

The initiation, step a) of the method according to the invention, will in many applications be performed by the addition to the fluid of at least one initiator. The initiator induces a polymerization/coagulation of polymerizable/coagulable components in the fluid that would otherwise not occur, or will promote the polymerization/coagulation to occur much more rapidly than would otherwise be the case. Within the scope of the invention, it is conceived that one or several of these initiators are immobilized on or in some other way associated to the film of electrically conducting material that is mentioned in step b). The initiator or initiators immobilized or associated to the film will from this position directly or indirectly initiate the polymerization/coagulation of the fluid.

The fluid to be analyzed by the method of the invention can be of many different kinds. It can be a pure polymerizable/coagulable component as for example pure styrene, methyl methacrylate, vinyl chlorid, acryl amide or acrylic acid. The fluid may also be some organic or inorganic solvent, as for example acetone, methyl ethyl ketone, tetrahydrofuran, methyl chloride or water, in which polymerizable components such as styrene, methyl methacrylate, acrylonitrile, acrylic acid, acryl amide and ethylene oxide are dissolved. The fluid can also be a technical fluid such as paint, lacquer, glue, thermosetting plastic or thermo-plastic, acryl amide or agarose. The fluid can further be a food stuff including sauces, custards, mousses, and jellies.

In some embodiments of the invention, the fluid is a biological fluid such as blood, blood plasma, milk, lymph, sperm and synovial fluid in which polymerizable/-coagulable components such as fibrinogen casein and thrombocytes are dissolved.

In a preferred embodiment of the invention the biological fluid is blood or blood plasma. The blood or blood plasma may be mixed with at least one coagulation inhibitor and/or at least one coagulation initiator, whereby the effects of such additions on qualitative and optionally quantitative occurrence of coagulation can be determined. The effects of such additions on the qualitative and quantitative occurrence of coagulation may be of considerable laboratory diagnostic importance. The added coagulation inhibitor is e.g. selected from the group consisting of heparin, hirudin, anti-thrombin, tissue factor pathway inhibitor, C1-inhibitor and Ca2+ activity lowering agent. The added coagulation initiator is e.g. selected from the group consisting of negatively charged surfaces including silica and ellergic acid derivatives; phospholipids; thromboplastin; endothelial cells and cell membranes; thrombocytes and their cell membranes; monocytes and their cell membranes; and any required coagulation factor lacking from the fluid.

The use of specially prepared or collected blood and blood plasma, in which the occurrence of qualitative and optionally qualitative coagulation is altered due to low levels of certain initiator(s) and/or inhibitor(s), allows embodiments of the invention that indirectly determine these initiators(s) and/or inhibitors(s). Determination is accomplished by adding samples containing the initiator(s) and/or inhibitor(s) to the specially prepared or collected blood or blood plasma. Total or partial restoration of the altered quantitative and optionally quantitative occurrence of coagulation in the specially prepared blood or blood plasma, as determined by the invention, by the addition of sample containing the initiator(s)/inhibitor(s) in question will indirectly determine levels of the initiator(s) and/or inhibitor(s) in the sample.

In other embodiments of the invention, the fluid to be analyzed is a polymerization reaction fluid. The fluid may comprise polymerizable components of one or several different kinds as disclosed above. Examples of polymerization reaction fluids include paints, lacquers, glues, thermosetting plastics, thermoplastics, acryl amide, agarose, food stuff including sauces, custards, mousses, jellies and sugars.

The film of electrically conducting material, disclosed in step b) of the method of the invention, is composed of at least one member selected from the group consisting of gold, silver, platinum, aluminum and electrically conducting polymer.

Preferably the thickness of the film is between 10 and 1000 nm.

The film support, also disclosed in step b) of the method of the invention, is of glass or plastics and has the form of a plate, half sphere, half spherical rod, optical fiber, beaker, cuvette, test tube or reactor window.

The changes in the reflected beams due to changes in the surface plasmon resonance angle measured in step d) (and e)) of the method of the invention are selected from the group consisting of polarization changes in relation to the polarization of the incident beams, and intensity changes.

These changes are measured with an appropriate instrument such as the surface plasmon resonance apparatus supplied by Biacore AB, Uppsala, Sweden, the principles of which has been described by Liedberg B. and Lundström I. (ibid.)

The invention will now be illustrated with reference to the description of experiments and the accompanied drawings, but it should be understood that the scope of protection is in no way limited to the experiments made.

SHORT DESCRIPTION OF THE DRAWINGS

DESCRIPTION OF EXPERIMENTS

Methods and Materials

All surface plasmon resonance (SPR) experiments were performed on a modified prototype of BIAlite, Pharmacia Biosensor, now Biacore AB, Stockholm, Sweden. The instrument was modified by re-orientating the detection unit, which was placed in a horizontal position in order to enable placement of sensor surfaces directly on the optointerface. The detection principle is thoroughly described by Liedberg B. and Lundström I. (ibid.) In the instrument used, shifts in the surface plasmon resonance angle are expressed in arbitrary resonance units (RU), where 1000 RU corresponds to a shift of about 0.1 degrees. The results are presented as so-called sensograms wherein the response in arbitrary resonance units (RU) is plotted against time (seconds).

Gold surfaces (films) were prepared by sputtering of 45 nm Au onto glass slides (Biacore AB, Uppsala, Sweden). The surfaces were cleaned in ozone prior to use, yielding a hydrophilic surface of contact angle <20°.

Citrated plasma was mixed from 2 apparently healthy donors. The plasma was stored at −70° C. and after thawing kept in refrigerator, and used within 4 hours.

Thromboplastin (GHI 113, 2500 U/ml) was from Global Hemostasis Institute MGR AB, Linköping, Sweden, $CaCl_2$ (20 mM) from Sigma, heparin from LEO, Denmark (5000 U/ml), and all reagents were stored refrigerated. All dilutions were made in Hank's buffered saline.

Experimental conditions

All experiments were performed at room temperature (22° C.). Reagents were thawed immediately prior to use and used without further heating. Refrigerated reagents were used without heating. The gold surfaces were cleaned within 1 hour prior to use in order to assure proper spreading of test fluid on the surface.

EXAMPLE 1.

A drop of whole blood, about 50 μL, obtained by skin puncture of a finger tip of an apparently healthy volunteer, was transferred with a plastic pipette tip onto a 45 nm gold film covered with dry immobilized thromboplastin, a coagulation initiator, see materials. The gold film was supported on a glass slide which was placed on the flat side of the semi-spherical rod prism of the modified BIAlite surface plasmon resonance instrument. The prism and the slide with the gold film were temperature equilibrated at 22° C. A instrument run, with continuous registrations of shifts in surface plasmon resonance angel, was started some minutes prior to applying the drop of blood.

Figure 1:
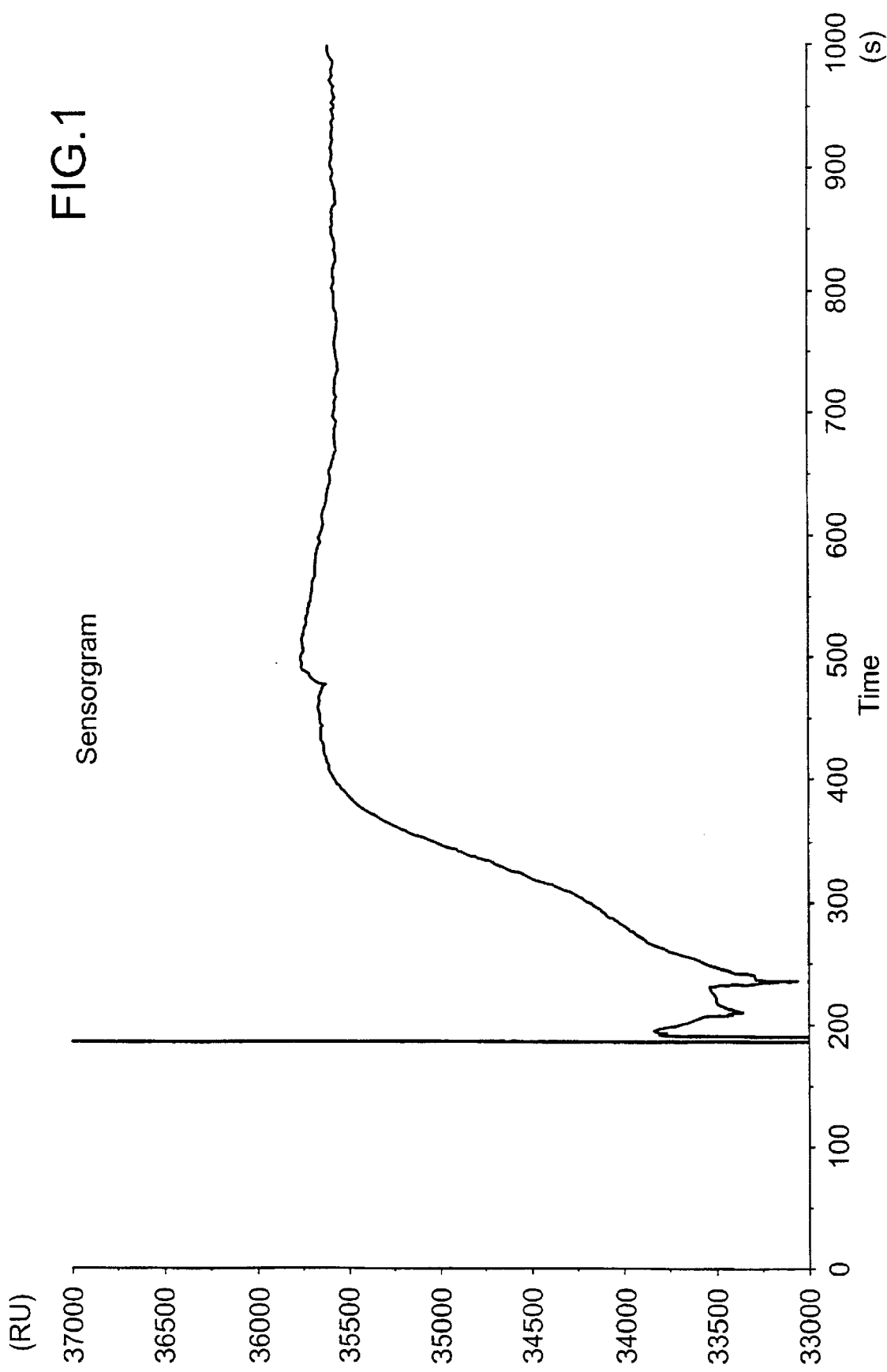
FIG. 1 shows a diagram, so-called sensogram, of coagulation in a drop of whole blood, initiated by immobilized thromboplastin. The instrument response (shift in surface plasmon resonance angle) expressed in resonance units (RU) is plotted against time.

FIG. 1 shows a diagram, so-called sensogram, wherein the response (shift in surface plasmon resonance angle) expressed in resonance units (RU) is plotted against time.

The sensogram is interpreted as follows: Application of the drop of blood on the gold film results in large changes in instrument readout, the vertical line at about 180 seconds. The readout then stabilizes at about 33500 RU. At about 240 seconds, the readout starts to increase and increases continuously for some minutes reaching a plateau of about 35500 RU at about 400 seconds. In total, during the time period 240 to 400 seconds, the readout increases by about 2000 RU. This relatively large increase, referred to as a relatively large signal, is caused by coagulation of the blood and is related to the magnitude of this coagulation. In separate experiments the coagulation was confirmed by touching the drop of blood on the gold film with the tip of a plastic pipette. At 240 seconds the drop of blood was liquid, but at 400 seconds the drop of blood was coagulated, i.e. was transformed into a gel.

The example clearly demonstrates that the occurrence of coagulation in whole blood, initiated by immobilized thromboplastin, is readily qualitatively and optionally quantitatively determined by the method of the invention.

EXAMPLE 2.

The method of the invention will indirectly determine the concentration of an initiator in a sample, here exemplified by thromboplastin in physiological saline solution. The samples indirectly analyzed contained 100, 10, 1, 0.1 and 0 U/mL of thromboplastin. Of these samples, 8 $\mu$L were mixed with 92 $\mu$L citrated human plasma. As this is an example of how the present invention can be applied to indirectly measure the concentration of initiator, the thromboplastin solutions and the citrated plasma may be regarded as test samples and reagent solution, respectively. From this point of view, the above mixture of thromboplastin solutions and citrated plasma are sample-reagent mixtures. To start the processes in the sample-reagent mixtures, the $Ca^{2+}$ activity of the mixture needs to be raised to coagulation permissible levels. In the experiment below, this is accomplished by mixing one part sample-reagent solution with one part 20 mM $CaCl_2$ solution. The addition of this later solution will thus start the coagulation process.

Of the described sample-reagent mixtures, 20 $\mu$L was placed on a 45 nm gold film on the semi-spherical rod prism of the modified BIAlite surface plasmon resonance instrument. An instrument run was started and 15 seconds later 20 $\mu$L of 20 mM $CaCl_2$ were added to, and mixed with, the 20 $\mu$L sample-reagent mixture already on the gold film.

Figure 2:
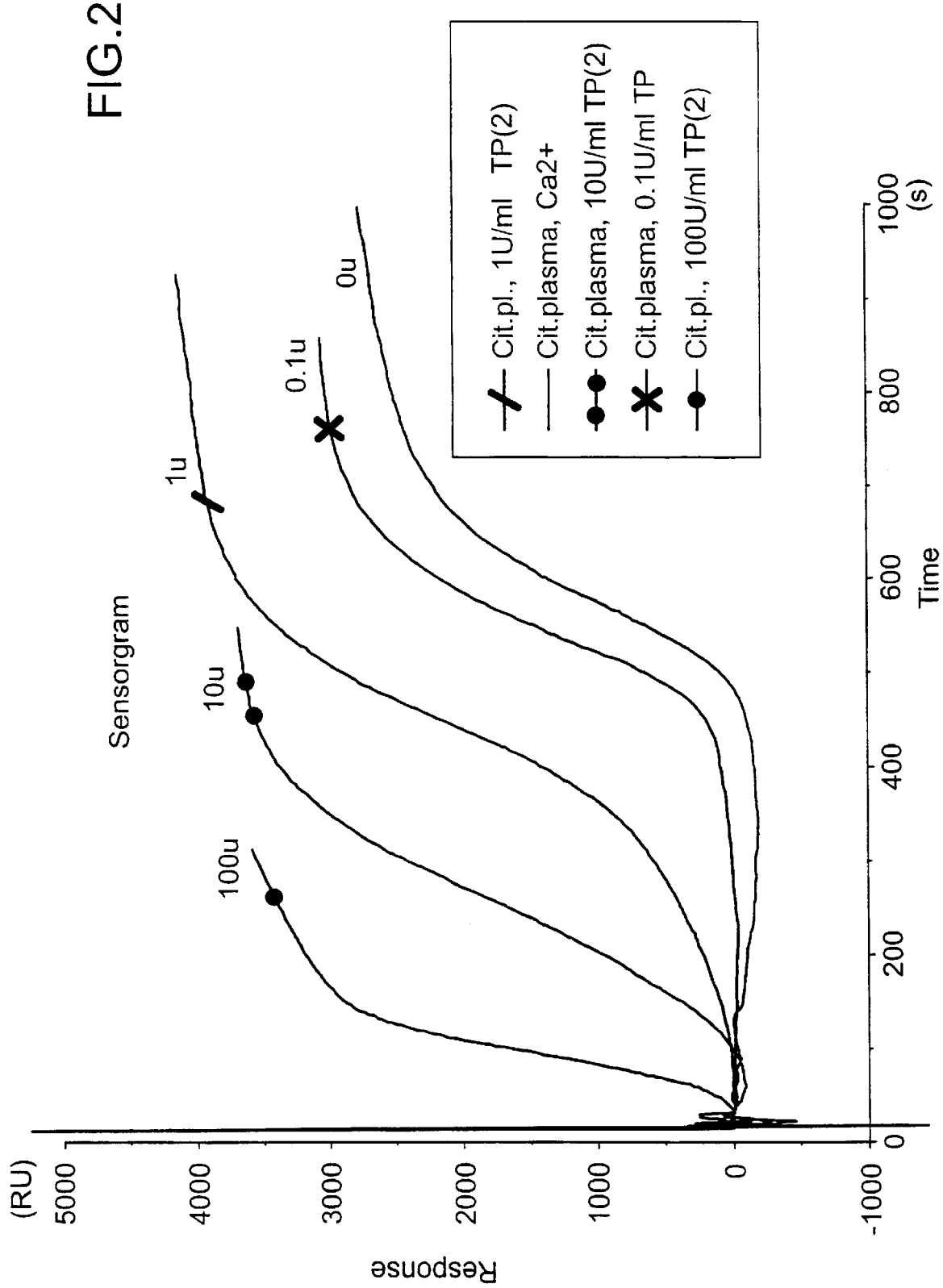
FIG. 2 shows a diagram, so-called sensogram, from which coagulation time can be determined for several samples with various thromboplastin levels. Each sample is mixed with citrated blood plasma and the coagulative reactions started by addition of calcium chloride solution the results show that thromboplastin levels in a sample can be determined by analysis according to the invention.

FIG. 2 shows diagrams, so-called sensograms, wherein the responses (shift in surface plasmon resonance angle) expressed in resonance units (RU) are plotted against time for the various sample. The diagrams are denoted 0, 0.1, 1, 10 and 100 U/mL for samples with corresponding thromboplastin concentration.

The sensograms are interpreted as follows: With 0 U/mL of sample thromboplastin, a relatively stable base line is observed for about 500 seconds followed by a sharp RU increase as the reaction mixture coagulates. The RU increase starts at about 520 seconds. This is identified as the spontaneously induced coagulation time of the re-calcified plasma. For the other samples, the registered tracing shows similar pattern; first a base-line and then a sharp RU increase as the mixture coagulates. The coagulation time, however, decreases, in a dose-dependent way, with increasing thromboplastin concentration. For samples with 0.1, 1, 10 and 100 U/mL thromboplastin the coagulation time is about 480, 380, 200 and 80 seconds, respectively. A plot of coagulation time against the logarithm of the sample thromboplastin concentration helps to convince that the present invention can be used to device an analytical system for qualitative determination of thromboplastin concentrations above 0.1 U/mL and quantitative determination of thromboplastin in the range 0.1 to 100 U/mL.

This example demonstrates the present invention can be used to indirectly determine the concentration of initiator(s).

EXAMPLE 3.

This example demonstrates the used of the analytical method of the invention for monitoring, in real-time, the synthesis (polymerization) of a plastic. The synthesis of a thermosetting plastic, namely the formation of crosslinked polyacryl amide in water solution, is monitored in the example.

The following solutions A, B and C are prepared.

Solution A: a mixture of 12 mL of 1 M HCl, 23 mL of TEMED and 25 mL of water.

Solution B: 7.5 g acryl amide and 0.2 g bis-acryl amide dissolved in 25 mL water.

Solution C: 0.35 g ammonium persulphate dissolved in 25 mL water.

A surface plasmon resonance instrument run is started. A reaction mixture is prepared by mixing 1 mL of solution A, 2 mL of solution B, 1 mL of water an 4 mL of solution C. Immediately after solution C is added and mixed, one drop, about 50 $\mu$L, of the reaction mixture is transferred to the gold film on the glass support of the instrument. Changes in the reflected beams due to changes in surface plasmon resonance angle are measured continuously. The changes are expressed in arbitrary units, RU, and registered as a function of time. The results are shown in FIG. 3.

Figure 3:
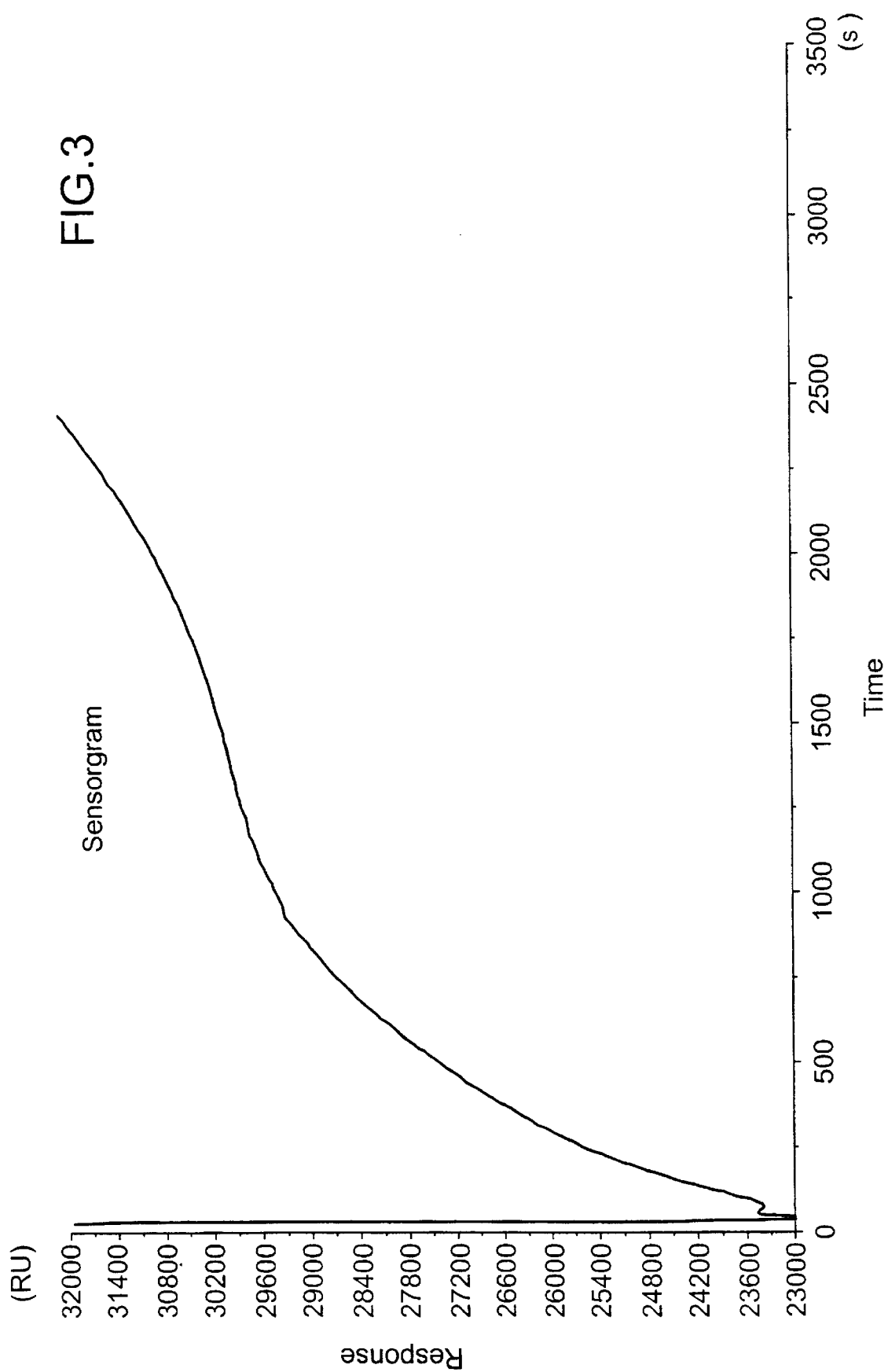
FIG. 3 shows a diagram, so-called sensogram, wherein a fluid containing acryl amide, a polymerizable component, is continuously monitored for qualitative and quantitative occurrence of polymerization.

FIG. 3 shows a diagram, so-called sensogram, wherein the polymerization reaction fluid, containing the polymerizable components acryl amide and bis-acryl amide, is continuously determined (monitored) for qualitative and quantitative occurrence of polymerization. The instrument responses (shift in surface plasmon resonance angle) expressed in resonance units (RU) is plotted against time.

The sensogram is described and interpreted as follows: A vertical line is seen in the plot at about 50 seconds. This is when the drop of reaction mixture is transferred to the gold film. Within a few seconds after the transfer, the instrument readout is stabilized to a baseline at about 23400 RU. At about 100 seconds the readout starts to increase. The rate of increase is at first rapid but looses speed continuously. At 1000 seconds the rate of increase is low and about constant. The readout is then reached about 29400 RU or about 6000 RU above baseline. At 2000 seconds the readout is about 30200 RU and continues to increase.

The baseline represents the non-reacted reaction mixture. The occurrence of polymerization is indicated by an increase in instrument readout which increases as the polymerization progresses. The fall in the rate of readout-increase indicates that the polymerization approaches completion at 1000 seconds. The continued increase after 2000 seconds may be due to movements, creeping, within the polymer perhaps caused by evaporation, i.e. drying of the polymer gel.

The example shows that the present invention can be used to determine qualitative and quantitative occurrence of polymerization of polymerizable components in a fluid. Since the instrument readout is continuous and the provided information simultaneous with the occurrence, 'real time', the analytical method of the invention appears most suitable for monitoring polymerization reactions.

We claim:

1. Analytical method of qualitative and optionally quantitative determination of occurrence of polymerization/coagulation in a fluid containing polymerizable/coagulable components, which comprises the steps of
   a) bringing the fluid or a sample thereof into contact with a film of electrically conducting material on a support which support is transparent for electromagnetic radiation used in step b) and which support is more optically dense than the fluid,
   b) directing incident beams of electromagnetic radiation through the support and the film, at angles equal to or greater than a critical angle for total reflection,
   c) measuring changes in reflected beams due to changes in the surface plasmon resonance angle,
   d) repeating steps b) and c) at least once,
   e) registering occurrence and magnitude of the changes measured in c), and
   f) determining the qualitative and optionally quantitative occurrence of polymerization/coagulation in the fluid by correlating the registered occurrence and magnitude of changes in e) with reference values.

2. Analytical method according to claim 1, wherein steps a) and b) are performed simultaneously or in an alternative order.

3. Analytical method according to claim 1, wherein step d) is repeated continuously.

4. Analytical method according to claim 1, wherein the polymerization/coagulation occurs spontaneously in the fluid.

5. Analytical method according to claim 1, wherein the polymerization/coagulation is initiated in the fluid by change of one or several conditions within the fluid selected from the group consisting of temperature, pressure, ionic strength, pH and redox potential.

6. Analytical method according to claim 1, wherein the polymerization/coagulation is initiated by addition of at least one reaction initiator to the fluid.

7. Analytical method according to claim 6, wherein the at least one initiator is attached to that surface of the film which is in contact with the fluid.

8. Analytical method according to claim 1, wherein the fluid is a biological fluid.

9. Analytical method according to claim 8, wherein the biological fluid is blood or blood plasma.

10. Analytical method according to claim 9, wherein the blood or blood plasma is mixed with at least one coagulation inhibitor and/or at least one coagulation initiator.

11. Analytical method according to claim 10, wherein the coagulation inhibitor is selected from the group consisting of heparin hirudin, anti-thrombin, tissue factor pathway inhibitor, C1-inhibitor and ca2+ activity lowering agent; and the coagulation initiator is selected from the group consisting of negatively charged surfaces; phospholipids; thromboplastin; endothelial cells and their cell membranes; Thrombocytes and their cell membranes; monocytes and their cell membranes; and any required coagulation factor lacking from the fluid.

12. Analytical method according to claim 1, wherein the fluid is a polymerization reaction fluid.

13. Analytical method according to claim 12, wherein the polymerization reaction fluid is a member of the group consisting of non-stiffened paints, lacquers, glues, thermo-setting plastics, thermo-plastics, acrylamide, agarose, and food stuff.

14. Analytical method according to claim 1, wherein the film of electrically conducting material is composed of at least one member selected from the group consisting of gold, silver, platinum, aluminum and electrically conducting polymers.

15. Analytical method according to claim 14, wherein a thickness of the film is between 10 and 100 nm.

16. Analytical method according to claim 1, wherein the film support is made of glass or plastics and has a form of a plate, half sphere, half spherical rod, optical fiber, beaker, cuvette, test tube or reactor window.

17. Analytical method according to claim 1, wherein the changes in the reflected beams due to changes in the surface plasmon resonance angle are selected from the group consisting of polarization changes in relation to polarization of the incident beams, and intensity changes.

18. Analytical method according to claims 1, wherein a wavelength of the incident light is chosen to coincide with the absorption wavelength(s) of the fluid.

19. Analytical method according to claim 11, wherein the negatively charged surfaces are selected from silica and ellergic acid derivatives.

20. Analytical method according to claim 13, wherein the food stuff is selected from the group consisting of sauces, custards, mousses, jellies, and sugars.

* * * * *